United States Patent [19]

N'Guyen et al.

[11] Patent Number: 5,516,507

[45] Date of Patent: May 14, 1996

[54] DERMATOLOGICAL GLUTATHIONE ALKYL ESTER COMPOSITION AND A PROCESS FOR TOPICAL TREATMENT

[75] Inventors: Quang L. N'Guyen, Antony; Alex Junino, Livry-Gargan; Christian Colin, Paris; Albert Lindenbaum, Versailles; Catherine Loufrani, Le Perreux Sur Marne, all of France

[73] Assignee: L'Oreal, Paris, France

[21] Appl. No.: 237,924

[22] Filed: May 4, 1994

[30] Foreign Application Priority Data

May 7, 1993 [FR] France .................................. 93 05513

[51] Int. Cl.$^6$ .................................................. A61K 7/42
[52] U.S. Cl. ................................. 424/59; 514/844
[58] Field of Search ......................... 514/844; 424/59, 424/60

[56] References Cited

FOREIGN PATENT DOCUMENTS 1092020  4/1955  France .
92/19224 11/1992  WIPO .

OTHER PUBLICATIONS

Photomed. Photobiol (1992) vol. 14, pp. 161–165, Hanada et al.
Chemical abstracts, 1974, vol. 79:149287, abstract of Japanese Patent 4800/505.

Katsumi Hanada et al., "Photoprotective Effect of Gluthathione Isopropyl Ester Against UVB Injury in the Mouse Skin;" Photomedicine and Photobiology, vol. 14, 1992, pp. 161–165.

Chemical Abstract, vol. 103, No. 9, Sep. 2, 1995, Abstract No. 67541r.

Database WPI, Derwent Publications Lts., Week 9138 (JP3-184,922).

Chemical Abstracts, vol. 102, No. 2, Jan. 14, 1985, Abstract No. 12207k.

Primary Examiner—Shelley A. Dodson
Attorney, Agent, or Firm—Oliff & Berridge

[57] ABSTRACT

A process for topical treatment of cutaneous ageing involves applying to skin a cosmetic or dermatological composition containing, as an active ingredient, a glutathione alkyl ester. The glutathione alkyl ester corresponds to the formula:

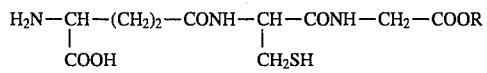

in which R represents an alkyl radical having from 1 to 10 carbon atoms.

10 Claims, No Drawings

DERMATOLOGICAL GLUTATHIONE ALKYL ESTER COMPOSITION AND A PROCESS FOR TOPICAL TREATMENT

FIELD OF THE INVENTION

The subject of the present invention is directed to a process for the topical treatment of cutaneous ageing which comprises applying to the skin a cosmetic or dermatological composition containing as active ingredient a glutathione alkyl ester.

It is known that the mechanisms for protection of the skin, especially against ultraviolet-type oxidative stresses, involve a number of cutaneous enzymes for detoxification such as catalases and glutathione peroxidases. Although the mechanisms are particularly complex and are only partially elucidated, they involve, in a well known manner, the following reactions:

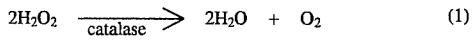

ROOH=hydrogen or organic peroxide
GSH=reduced glutathione
GSSG=oxidized glutathione
ROH=water or alcohol
Gpx=
- selenodependent glutathione peroxidase when the substrate is hydrogen peroxide or an organic peroxide,
- gluthathione transferase when the substrate is an organic peroxide,
- these enzymes are grouped under the generic term of glutathione peroxidase.

Catalases and glutathione peroxidases, through their involvement in the anti-radical process, therefore play an essential role in the mechanisms for protection of the skin, but their activity is affected by a prolonged oxidative stress.

In order to restore total catalase activity, an addition of exogenous catalase would probably be effective, but is unfortunately banned in cosmetics.

Moreover, the use of glutathione alkyl enters as agents which make it possible to increases the intracellular level of glutathione after treatment with an agent inhibiting the synthesis of endogenous glutathione, as well as their possible use as cell-protecting agent, has been described in U.S. Pat. No. 4,879,370.

However, this document describes only the intraperitoneal uses of glutathione alkyl esters for therapeutic purposes.

After numerous studies, it has now been observed, surprisingly and unexpectedly, that by using a glutathione alkyl ester by topical application, cutaneous ageing could be limited by acting conjointly on the different enzymes involved in the mechanisms of detoxification.

SUMMARY OF THE INVENTION

The present invention relates to a process for the topical treatment of cutaneous ageing by applying to skin an effective amount of a cosmetic or dermatological composition containing glutathione alkyl ester, as an active ingredient. The glutathione alkyl ester corresponds to the following formula:

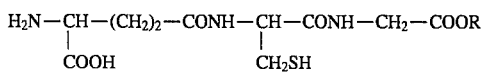

in which R represents an alkyl radical having from 1 to 10 carbon atoms.

DESCRIPTION OF PREFERRED EMBODIMENTS

The subject of the present invention is therefore a process for the topical treatment of cutaneous ageing which comprises applying to the part of the skin to be treated a sufficient amount of a cosmetic or dermatological composition containing an active ingredient an effective amount of a glutathione alkyl ester corresponding to the formula:

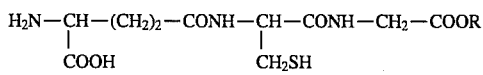

in which: R represents an alkyl radical having from 1 to 10 carbon atoms.

The expression "cutaneous" should be understood to means not only the skin but also the scalp as well as the mucous membranes.

According to the invention, the glutathione alkyl ester used is preferably glutathione monomethyl ester, monoethyl ester or monooctyl ester.

Glutathione monoalkyl esters can be prepared according to known methods, especially according to the process described in U.S. Pat. No. 4,879,370, or alternatively by the biotechnological route.

The glutathione alkyl ester is used according to the invention in the preparation of the said composition at a concentration of between 0.01% and 10%, and preferably between 0.5 and 5% by weight relative to the total weight of the composition.

According to a particular embodiment of the invention, the glutathione alkyl ester is used in combination with an additional active ingredient which is present in the composition at a concentration of between 0.01 and 10% by weight relative to the total weight of the composition.

This additional active ingredient an be chosen from all the active ingredients commonly used in cosmetology or in dermatology, in particular those having a superoxide anion dismutation activity such as for example superoxide dismutase (SOD).

The expression "SOD" is understood to mean any component with superoxide dismutase activity, namely any enzymes which can catalyse a dismutation reaction as well as any other product having this activity, which includes especially the SODs modified by grafting of polyalkylene oxide, polyethylene glycol, polysaccharide or acylated groups as well as the substances containing such products. There may be mentioned, in this respect, European Patent Application No. EP 223.257.

The SOD which can be used according to the invention can thus be modified especially according to the teaching given in "International Conference on Medical, Biochemical and Chemical Aspects of Free Radicals" (Apr. 9–13, 1988 Kyoto) p. 317 of the article by H. Morimoto, or according to the teaching of M. Yukio Ando, p. 318 (same source), or alternatively according to Japanese Patent Applications JP 01240304 and JP 02273176, European Patent Applications EP 426 488 and 424 033 and U.S. Pat. No. 5,006,333.

The SOD which can be used according to the invention can, in addition, be used in a form stabilized by means of known techniques, for example based on phosphate, in the presence of alkali metal chloride and sucrose, as published for example in French Patent FR 2,634,125.

Among the substances having an SOD-type activity, there may also be mentioned copper 3,',5'-diisopropylsalicylate whose use has been described in European Patent Application EP 293.579.

All the superoxide dismutases described above, as well as the variants and equivalents which a person skilled in the art can deduce from this literature, are suitable as SODs which can be used according to the invention. They can be various origins.

There may be especially mentioned the SODs of animal (for example bovine, porcine, and the like), human (for example placenta, blood, and the like) or plant (for example fungi, algae, spinach, and the like) origin. They can also be obtained from bacterial or yeast, or alternatively by the biotechnological route (for example genetic engineering and the like).

Among the examples of SOD of bovine origin, there may be mentioned in particular the Cu-Zn type SOD which has been purified to homogeneity and approved for clinical applications (New Trends in Allergy, I. Ring et al., Ed. Springor Verlag 1986).

Among the examples of SOD obtained by the biotechnical route, especially from cultures of bacteria, yeasts, animal cells and the like, there may be mentioned the recombinant human Cu-Zn SOD from the company UBE Industries Ltd.

Among the examples of SODs extracted from bacteria, there may be mentioned in particular those extracted from *Escherichia coli*; among the superoxide dismutases extracted from fungi, there may be mentioned in particular those extracted from *Pleurotus olearius*; among the superoxide dismutases extracted from blood, there may be mentioned erythrocupreines.

There may also be mentioned the superoxide dismutases extracted from marine bacterial strains, such as for example strains of *Photobacterium phosphoreum, Photobacterium leiognathi* or *Photobacterium sepia*.

Among the various strains which can be used, there may be mentioned the strains of *Photobacterium phosphoreum* No. ATCC 1140, of *Photobacterium leiognathi* No. ATCC 25521, of *Photobacterium sepa* No. ATCC 15709, of *Escherichia coli* No. ATCC 15224 and of *Pleurotus clearius* Gillet (Cryptogamy Laboratory of Paris).

The SODs which can be used according to the invention can also be prepared by application of the methods already described for example in the article by Koole et al. (*J. Biol. Chem.*, 245, p. 6176, 1970) as well as in Eur. J. Rheumatol. and Inflammation, 4, 173–182 (1982).

The SOD enzymatic activity values of the present invention have all been expressed in units according to MacCord and Fridovitch [*J. Biol. Chem.* 244, 6049 (1969)].

Thus, it has been possible to determine, regardless of the origin of the SOD, that the preferred sufficient quantity of SOD per 100 g of composition is that which corresponds to an activity of about 30 units to about 1000 units in the composition. But generally, the SOD may possess from 10 units to 5000 units per 100 g of composition.

The compositions according to the invention may also comprise, in combination with the glutathione alkyl esters, compounds chosen from chelators of metals and in particular of free iron, such as the phosphonic derivatives described in French Patent Application FR 91.05464 (Publication No. 2,675,997), the derivatives of EDTA, of DTPA, desferal, lactoferrin, transferrin, ferritin or phytic acid.

The compositions based on a glutathione alkyl ester which are used in the treatment of cutaneous ageing are provided in the form of aqueous solutions such as sera, lotions, gels, ointments, emulsions of the cream or milk type, pastas, as well as systems based on vesicular dispersions or dispersions of nanocapsules as described in French Patent Application No. 90.03418 (Publication No. 2,659, 554).

In this latter form, the vesicles contain for example at least one active ingredient as described above, incorporated in micelles or lipid double layers, encapsulating an aqueous phase.

The compositions according to the invention may also be provided in the form of powder, solid sticks or can be packaged in pressurized bottles and can be applied in the form of foams or sprays.

These compositions based on a glutathione alkyl ester which are used in the treatment of cutaneous ageing may comprise, in addition, ingredients and adjuvants normally used in the preparation of cosmetic or dermatological compositions, such as silicones, thickening agents, surfactants, polymers, solid fatty substances such as for examples waxes or lanolin, sequestering agents, colourants, perfumes, ultraviolet-absorbing substances, self-tanning agents such as dihydroxyacetone, as well as solid fillers such as powders or pigments.

Among the pigments which can be used according to the invention, there may be mentioned melanin, whether of natural origin, for example derived from hair or cephalopod ink, or of synthetic origin, pigments resulting from oxidative or enzymatic polymerization of precursors such as L-tyrosine, L-dopa, catechol and their derivatives, or alternatively pigments of metallic oxides such as titanium, zinc, cerium or zirconium oxides.

When the compositions according to the invention contain the said pigments of metallic oxides, the latter are present at a concentration of between 0.1 and 15% and preferably between 0.5 and 10% by weight relative to the total weight of the composition.

These pigments are preferably used in the form of nanopigments, of average diameter of less than 100 nm, and in particular of between 5 and 50 nm.

These pigments can also be coated with compounds such as amino acids, anionic surfactants, lecithins, fatty alcohols, beeswax, fatty acids, salts of fatty acids especially of sodium, potassium, zinc, iron or aluminium, metallic alkoxides especially of titanium or aluminium, polyethylene, silicones, proteins especially collagen or elastin, alkanolamines, silicon oxides, metallic oxides or sodium hexametaphosphate.

The anti-ageing compositions according to the invention can be used not only for skin care as well as for its protection, but also find direct application in anti-sun products and in make-up products.

The anti-ageing compositions according to the invention can also be used on the scalp for slowing down hair loss and for promoting hair regrowth. These compositions may contain in combination some active compounds such as "Minoxidil" (2,4-diamino-6-piperidino-pyrimidine 3-oxide) and its derivatives, diazoxide (7-chloro-3-methyl-1,2,4-benzothiadizine 1,1-dioxide) and "Phenytoin" (5,5-diphenyl-2, 4-imidazolidinedione).

The compositions according to the invention can, in addition, find a dentibuccal use, in particular in the form of toothpastes. In this case, the composition comprises customary adjuvants and additives for compositions for buccal use and especially surfactants, thickening agents, humectants and polishing agents such as silica, active agents such as fluorides, and in particular sodium fluoride and optionally sweeteners such as sodium saccharinate.

Several examples of compositions according to the invention will now be given by way of illustration.

EXAMPLE 1

Anti-ageing Cream for the Face

A. Fatty phase

| | |
|---|---|
| Polyethylene glycol monostearate 50 EO (ICI) | 1.5% |
| Mixture of diglycerol mono- and distearate | 1.5% |
| Vaseline oil | 24% |
| Cetyl alcohol | 2.5% |

B. Aqueous phase

| | |
|---|---|
| Glutathione monoethyl ester | 0.5% |
| Water q.s. | 100% |

(In this example as well as in the following examples, the percentages are expressed by weight relative to the weight of the final composition).

The cream is prepared in the following manner:

The fatty phase A is heated to 80° C. and then the aqueous phase B is poured into it, with vigorous stirring.

The cream obtained has a very nice appearance and has good cosmetic properties when it is applied to the face.

EXAMPLE 2

Anti-ageing Treatment Fluid for the Body

A carrier is first prepared, in a know manner, in the form of a dispersion of lipid spherules, of the following composition (in % relative to the final composition):

| | |
|---|---|
| Non-ionic amphiphilic lipid of formula $R-(O-CH-CH_2)_n-OH$ $\quad\quad\quad\quad\quad\mid$ $\quad\quad\quad\quad CH_2OH$ in which R is a hexadecyl radical and n has an average statistical value equal to 3 | 4.5% |
| Cholesterol | 4.5% |
| Dicetyl phosphate | 1.0% |
| Methyl para-hydroxybenzoate | 0.3% |
| Sterile demineralized water | 30% |

For that, the first three ingredients are mixed by melting at 100° C., under a nitrogen atmosphere; the mixture is cooled to 80° C. and then homogenized by means of a Virtis type ultradispersing device. Water and preserving agent are then added. After adjusting the dispersion to room temperature, 1% glutathione monoethyl enter is then added to it followed by the following phase A:

Phase A:

| | |
|---|---|
| Perfume | 0.4% |
| Sunflower oil | 10% |
| Paraffin oil | 4% |
| Vitamin E | 2% |
| Soya bean lecithin | 1% |
| Ascorbyl palmitate | 1% |
| Hexadecylamine salicylate | 0.2% |

The mixture is homogenized by means of an ultradispersing device and the following phase B is then dispersed:

Phase B:

| | |
|---|---|
| Cross-linked polyacrylic acid marketed under the name "Carbopol 940" by the company Goodrich | 0.4% |
| Demineralized water | 39.3% |

The whole is finally neutralized by means of 0.4% of triethanolamine.

The treatment fluid thus obtained can be used by application to the body to provide softness to the skin as well as an improvement of its appearance.

EXAMPLE 3

Protective Beauty Milk for the Body

The milk is provided in the form of an oil-in-water (O/W) emulsion having the following composition:

| | |
|---|---|
| Glutathione monoethyl ester | 1% |
| Purcellin oil (Dragoco) | 2% |
| Vaseline oil | 6% |
| Oleyl alcohol | 1% |
| Isopropyl myristate | 1.5% |
| Glycerine monostearate | 2% |
| Stearin | 1.4% |
| Cetyl alcohol | 0.1% |
| Perfume | 0.9% |
| Cross-linked polyacrylic acid marketed under the name "Carbopol 941" by the company Goodrich | 0.35% |
| Pure triethanolamine | 1.05% |
| Butyl para-hydroxybenzoate | 0.04% |
| Preserving agent | 0.3% |
| Propylene glycol | 5% |
| Moisturizing mixture (sodium lactate/ TEA lactate/serine/urea/lactic acid) marketed under the name "Hydroviton" by the company Dragoco | 1.5% |
| Colourant F.D.C. blue 1 (Kohnstamn) at 1% in water | 0.03% |
| Demineralized water q.s. | 100% |

EXAMPLE 4

Anti-ageing Cream for the Body

This cream is provided in the form of an O/W emulsion having the following composition:

| | |
|---|---|
| Glutathione monoethyl ester | 0.8% |
| Cetyl alcohol | 0.5% |
| Sipol wax | 5% |
| Glycerol monostearate | 1.5% |
| Vaseline oil | 6% |
| Isopropyl myristate | 3% |
| Glycerine | 10% |
| Perfume | 0.2% |
| Water q.s. | 100% |

EXAMPLE 5

Anti-ageing Cream for the Body

This cream is provided in the form of an O/W emulsion having the following composition:

| | |
|---|---|
| Glutathione monoethyl ester | 0.5% |
| Sipol wax | 6% |
| Glycerol monostearate | 1.5% |
| Sodium stearate | 0.8% |
| Vaseline oil | 6% |
| Isopropyl palmitate | 2% |
| Glycerine | 15% |
| Perfume | 0.3% |
| Water q.s. | 100% |

EXAMPLE 6

Anti-wrinkle Dermatopharmaceutical Gel

The following compounds are mixed at room temperature and with stirring:

| | |
|---|---|
| Glutathione monoethyl ester | 0.6% |
| Block polymer of polyoxyethylene/polyoxypropylene/polyoxyethylene "Poloxamer 182" marketed under the name "Synperonic PE/L62" by the company ICI | 0.2% |
| Propylene glycol | 4% |
| Lactic acid | 1% |
| Tetrasodium salt of ethylenediaminetetraacetic acid | 0.1% |
| Phenoxyethanol | 0.25% |
| Water q.s. | 100% |

1% "Carbopol 940" is added to the dispersion obtained followed by sodium hydroxide in sufficient quantity to adjust the pH to 5.

The gel obtained is applied to the face and the neck.

EXAMPLE 7

Anti-ageing Protective Treatment Cream

| | |
|---|---|
| Glutathione monoethyl ester | 0.7% |
| Mixture of cetylstearyl alcohol and oxyethylenated cetylstearyl alcohol containing 33 EO marketed under the name "Sinnowax AO" by the company Henkel | 5% |
| Glycerol stearate | 1% |
| Cetyl alcohol | 1% |
| Jojoba oil | 6% |
| Linoleic acid | 6% |
| Titanium oxide marketed under the name "MT 100 T" by the company Tayca | 5% |
| Preservative q.s. | |
| Water q.s. | 100% |

The fatty phase is heated to 80° C. and then titanium oxide is added. The aqueous phase is then poured, with stirring at 80° C., into the fatty phase.

This composition, in the form of a cream, is applied daily to the face in order to retard the appearance of wrinkles.

EXAMPLE 8

Anti-loss Serum for the Scalp

| | |
|---|---|
| Glutathione monoethyl ester | 0.20% |
| Polyglyceryl-2 stearate marketed under the name "Hostacerine DGS" by the company Hoechst | 1.30% |
| Cholesterol | 0.60% |
| Sodium salt of phosphatidic acid | 0.10% |
| Glycerine | 3.00% |
| L-hydroxyproline | 1.00% |
| D-panthenol | 1.50% |
| Guanosine | 0.01% |
| Preservatives | 0.30% |
| Polyphosphonate marketed under the name "Dequest 2046" by the company Monsanto Chemical | 0.80% |
| Lactic hydrolysate marketed under the name "Lactolan LS" by the Serobiological Laboratories of Nancy | 5.00% |
| Minoxidil | 1.00% |
| Ceruloplasmin | 0.01% |
| Aqueous solution of superoxide dismutase containing 5000 units/ml marketed by the company Pentapharm | 1.00% |
| Mixture of polycarboxyvinyl acids marketed under the name "Carbopol 940" by the company Goodrich | 0.50% |
| Triethanolamine q.s. pH 6.5 | |
| Demineralized water q.s. | 100% |

EXAMPLE 9

Anti-ageing Depigmenting Cream Based on Liposomes a) A dispersion of lipid vesicles is first prepared.

For that, the following ingredients are mixed by melting at 110° C. under a nitrogen atmosphere:

| | |
|---|---|
| Non-ionic amphiphilic lipid of formula $$R-(O-CH-CH_2)_n-OH$$ $$\phantom{R-(O-}|$$ $$\phantom{R-(O-C}CH_2OH$$ in which R is a hexadecyl radical and n has an average statistical value equal to 3 | 3.75% |
| Cholesterol | 3.75% |

After cooling the mixture to 90° C., there is added:

| | |
|---|---|
| 5-Heptanoyl-salicylic acid | 0.50% |

After homogenization by means of a Virtis-type ultradispersing device, the following ingredients are incorporated:

| | |
|---|---|
| Glycerine | 3.00% |
| Demineralized water | 19.30% |

The mixture is cooled to 70° C. and then homogenized, and there are added:

| | |
|---|---|
| Glutathione monoethyl ester | 0.60% |
| Kojic acid | 1.00% |
| Demineralized water | 22.42% |

The temperature of the mixture is reduced to 40° C., it is homogenized and the following products are finally added to it:

| | |
|---|---|
| Caffeic acid | 1.27% |
| Diethylene glycol monoethyl ether | 7.50% |

After homogenization, the dispersion obtained has lipid vesicles whose average size is about 0.2 microns.

b) The cream is then prepared.

For that, the following ingredients are added at 25° C. to the dispersion obtained earlier:

| | |
|---|---|
| Vaseline oil | 14.00% |
| Volatile silicone oil | 10.00% |

After homogenization by means of an ultradispersing device, the following products are incorporated:

| | |
|---|---|
| Perfume | 0.40% |
| Mixture of polycarboxyvinyl acids marketed under the name "Carbopol 940" by the company Goodrich | 0.40% |
| Triethanolamine | 1.50% |
| Methyl para-hydroxybenzoate | 0.20% |
| Demineralized water q.s. | 100% |

The cream thus obtained is beige in colour and has good cosmetic properties.

EXAMPLE 10

Anti-ageing and Anti-loss Gel for the Scalp

| | |
|---|---|
| Glutathione monoethyl ester | 0.20% |
| Superoxide dismutase | 30 IU |
| Polyphosphonate marketed under the name "Dequest 2046" by the company Monsanto Chemical | 0.07% AS |
| Propylene glycol | 5% |
| Ceruloplasmin | 0.01% |
| Cross-linked polyacrylic acid marketed under the name "Carbopol 941" by the company Goodrich | 0.50% |
| Minoxidil | 1.00% |
| Triethanolamine q.s. pH 7 | |
| Preservatives q.s. | |
| Water q.s. | 100% |

EXAMPLE 11

Treatment cream for the Face in the Form of an Oil-in-water Emulsion

| | |
|---|---|
| Glutathione monoethyl ester | 0.50% |
| Superoxide dismutase assaying at 3.13 U/mg q.s. 600 units marketed by the company Pentapharm | 0.20% |
| Oxyethylenated polyethylene glycol 50 | 1.50% |
| Monodiglyceryl stearate | 1.50% |
| Vaseline oil | 24.00% |
| Cetyl alcohol | 2.50% |
| Triethanolamine q.s. pH 7 | |
| Water q.s. | 100% |

A cream is prepared in the following manner.

the mixture of the ingredients, with the exception of SOD, is heated to 80° C., and then after homogenization and cooling of the mixture thus obtained to 30° C., the SOD is added.

EXAMPLE 12

Water-in-oil Emulsion

| | |
|---|---|
| Glutathione monooctyl ester | 0.5% |
| Polyethylene glycol 40 | 1.5% |
| Monodiglyceryl stearate | 1.5% |
| Vaseline oil | 24% |
| Cetyl alcohol | 2.5% |
| Sorbitan tristearate | 0.3% |
| Water q.s. | 100% |

EXAMPLE 13

Oil-in-water Emulsion

| | |
|---|---|
| Glutathione monomethyl ester | 0.5% |
| Polyethylene glycol 40 | 1.5% |
| Monodiglyceryl stearate | 1.5% |
| Vaseline oil | 24% |
| Cetyl alcohol | 2.5% |
| Glyceryl stearate | 1% |
| Water q.s. | 100% |

EXAMPLE 14

Water-in-oil Emulsion

| | |
|---|---|
| Glutathione monomethyl ester | 1% |
| Cetyl dimethicone copolyol | 3% |
| Bentone gel | 5% |
| Volatile silicone | 10% |
| Oil of karite butter | 5% |
| Purcellin liquid | 3% |
| Magnesium sulphate | 0.7% |
| Glycerol | 3% |
| Water q.s. | 100% |

By daily applying the above compositions of Examples 1 to 14 in a sufficient amount on the part of the skin to be treated during 2 to 5 weeks cutaneous ageing could be limited, the skin being softer and smoother than before treatment.

What is claimed is:

1. A process for the topical treatment of cutaneous ageing which comprises applying to the part of the skin to be treated an effective amount of a composition containing as active ingredient from 0.01 to 10% by weight relative to the total weight of the composition of a glutathione monoalkyl ester corresponding to the formula:

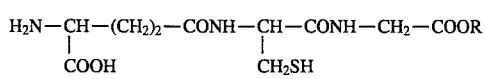

in which: R represents an alkyl radical having from 1 to 10 carbon atoms.

2. The process of claim 1, wherein said glutathione monoalkyl ester is glutathione monomethyl ester, monoethyl ester or monooctyl ester.

3. The process of claim 1 wherein said glutathione monoalkyl ester is present in the composition at a concentration of between 0.01% and 10% by weight relative to the total weight of the composition.

4. The process of claim 1, wherein said composition further contains an active ingredient selected from the group consisting of a superoxide dismutase of animal, human or plant origin, a superoxide dismutase grafter with polyalkylene oxide, polyethylene glycol, polysaccharide or acylated groups, a superoxide dismutase stabilized with phosphate and copper 3', 5'-diisopropyl salicylate.

5. The process of claim 4, wherein said active ingredient is present at a concentration of between 0.001 and 10% by weight relative to the total weight of the composition.

6. The process of claim 1 wherein said composition further comprises, at least one metal chelating agent.

7. The process of claim 1 wherein said composition further comprises metallic oxide pigments.

8. The process of claim 7, wherein said pigments are present in the composition at a concentration of between 0.1 and 15% by weight relative to the total weight of the composition.

9. A composition for the topical treatment of cutaneous ageing, comprising, in a suitable carrier for skin application, an effective amount of a glutathione mono-alkyl ester corresponding to the formula:

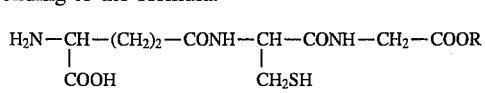

in which:

R represents an alkyl radical having 1 to 10 carbon atoms, said composition further comprising an active ingredient selected from the group consisting of a superoxide dismutase of animal, human or plant origin, a superoxide dismutase grafted with polyalkylene oxide, polyethylene glycol, polysaccharide or acylated groups, a superoxide dismutase stabilized with phosphate and copper 3', 5=-diisopropyl salicylate.

10. The composition of claim 9, wherein said glutathione mono-alkyl ester is present in a proportion of between 0.1 and 10% and said active ingredient in a proportion of between 0.001 and 10% by weight relative to the total weight of the composition.

* * * * *